(12) United States Patent
Karmaker et al.

(10) Patent No.: US 7,252,508 B2
(45) Date of Patent: Aug. 7, 2007

(54) ENDODONTIC OBTURATOR

(75) Inventors: Ajit Karmaker, Wallingford, CT (US); Arun Prasad, Cheshire, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 105 days.

(21) Appl. No.: 10/319,243

(22) Filed: Dec. 13, 2002

(65) Prior Publication Data

US 2004/0115589 A1    Jun. 17, 2004

(51) Int. Cl.
*A61C 5/02* (2006.01)
(52) U.S. Cl. .......................................... 433/224; 433/81
(58) Field of Classification Search ................ 433/81, 433/102, 224
See application file for complete search history.

(56) References Cited

U.S. PATENT DOCUMENTS

| | | | |
|---|---|---|---|
| 277,943 A | 5/1883 | Richmond | |
| 674,419 A | 5/1901 | Kinsman | |
| 1,312,120 A | * 8/1919 | Hurtt | ........................... 433/224 |
| 1,463,963 A | 8/1923 | Miller | |
| 1,469,992 A | 10/1923 | Card | |
| 1,641,844 A | 9/1927 | Fisher | |
| 1,649,508 A | 11/1927 | Carmichael | |
| 3,318,000 A | 5/1967 | Paris | |
| 3,504,438 A | 4/1970 | Wittman et al. | |
| 3,740,851 A | 6/1973 | Weissman | |
| 3,751,399 A | 8/1973 | Lee, Jr. et al. | |
| 3,813,779 A | 6/1974 | Tosti | |
| 3,855,702 A | 12/1974 | Malmin | |
| 3,899,830 A | 8/1975 | Malmin | |
| 3,919,774 A | 11/1975 | Fishman | |
| 3,949,479 A | 4/1976 | Malmin | |
| 3,968,567 A | 7/1976 | Nevins | |
| 4,050,156 A | 9/1977 | Chasanoff et al. | |
| 4,253,829 A | 3/1981 | Adelberger | |
| 4,253,835 A | 3/1981 | Ware | |
| 4,343,608 A | 8/1982 | Hodosh | |
| 4,407,675 A | 10/1983 | Hodosh | |
| 4,425,094 A | 1/1984 | Tateosian et al. | |

(Continued)

FOREIGN PATENT DOCUMENTS

DE    34 08 503 A1    9/1984

(Continued)

OTHER PUBLICATIONS

PCT Notification of Transmittal of the International Search Report or the Declaration with date of mailing Aug. 17, 2000.

(Continued)

*Primary Examiner*—Ralph A. Lewis
(74) *Attorney, Agent, or Firm*—Ann M Knab

(57) ABSTRACT

An endodontic obturator comprising a shaft section and a filler section fabricated of the same material and formed as a single unit. A handle section may be included and may be formed integrally with the shaft section and filler section as a single unit, or may be fabricated separately and attached to the single unit containing the shaft section and the filler section. An endodontic post is provided having a post section and a filler section fabricated of the same matrix material to provide a cohesive bond between the two sections.

48 Claims, 1 Drawing Sheet

U.S. PATENT DOCUMENTS

| | | | |
|---|---|---|---|
| 4,480,996 A | 11/1984 | Crovatto | |
| 4,480,998 A | 11/1984 | Carse | |
| 4,505,675 A | 3/1985 | Albert | |
| 4,505,676 A | 3/1985 | Gosner | |
| 4,518,356 A | 5/1985 | Green | |
| 4,525,147 A * | 6/1985 | Pitz et al. | 433/224 |
| 4,538,989 A | 9/1985 | Apairo, Jr. et al. | |
| 4,543,065 A | 9/1985 | Bushway | |
| 4,622,012 A | 11/1986 | Smoler | |
| 4,657,592 A | 4/1987 | Takubo | |
| 4,681,545 A * | 7/1987 | Lapcevic | 433/224 |
| 4,682,949 A | 7/1987 | Warrin | |
| 4,684,555 A | 8/1987 | Neumeyer | |
| 4,721,735 A | 1/1988 | Bennett et al. | |
| 4,738,616 A | 4/1988 | Reynaud | |
| 4,740,245 A | 4/1988 | Futami et al. | |
| 4,746,292 A | 5/1988 | Johnson | |
| 4,758,156 A | 7/1988 | Johnson | |
| 4,766,200 A | 8/1988 | Riazi | |
| 4,801,528 A | 1/1989 | Bennett | |
| 4,813,876 A | 3/1989 | Wang | |
| 4,820,152 A | 4/1989 | Warrin et al. | |
| 4,871,312 A | 10/1989 | Heath | |
| 4,882,407 A | 11/1989 | Riazi | |
| 4,931,096 A | 6/1990 | Fujisawa et al. | |
| 4,934,934 A | 6/1990 | Arpaio, Jr. et al. | |
| 4,936,775 A | 6/1990 | Bennett | |
| 4,936,776 A | 6/1990 | Kwiatkowski | |
| 4,950,697 A | 8/1990 | Chang et al. | |
| 4,952,150 A | 8/1990 | Schiwiora et al. | |
| 4,966,952 A | 10/1990 | Riaza | |
| 4,986,754 A | 1/1991 | Chang et al. | |
| 5,051,093 A | 9/1991 | Fitzmorris | |
| 5,064,373 A | 11/1991 | Staubli et al. | |
| 5,067,900 A | 11/1991 | McSpadden | |
| 5,073,112 A | 12/1991 | Weil | |
| 5,074,792 A * | 12/1991 | Bernadat | 433/220 |
| 5,083,923 A | 1/1992 | McSpadden | |
| 5,085,586 A | 2/1992 | Johnson | |
| 5,088,927 A | 2/1992 | Lee | |
| 5,089,183 A | 2/1992 | Johnson | |
| 5,092,773 A | 3/1992 | Levy | |
| 5,098,298 A | 3/1992 | Johnson | |
| 5,104,321 A | 4/1992 | Filhol | |
| 5,106,298 A | 4/1992 | Heath et al. | |
| 5,118,297 A * | 6/1992 | Johnson | 433/224 |
| 5,149,268 A * | 9/1992 | Johnson | 433/224 |
| 5,161,973 A | 11/1992 | Johnson | |
| 5,165,893 A | 11/1992 | Thompson | |
| 5,171,146 A | 12/1992 | Guerci | |
| 5,181,850 A | 1/1993 | Neumeyer | |
| 5,190,702 A | 3/1993 | Johnson | |
| 5,215,461 A | 6/1993 | Riazi | |
| 5,232,440 A | 8/1993 | Wilk | |
| RE34,439 E | 11/1993 | Heath | |
| 5,275,562 A | 1/1994 | McSpadden | |
| 5,286,193 A | 2/1994 | Roane | |
| 5,286,423 A | 2/1994 | Johnson | |
| 5,302,129 A | 4/1994 | Heath et al. | |
| 5,326,263 A | 7/1994 | Weissman | |
| 5,328,367 A | 7/1994 | Johnson | |
| 5,328,372 A | 7/1994 | Reynaud et al. | |
| 5,372,759 A | 12/1994 | Johnson | |
| 5,380,200 A | 1/1995 | Heath et al. | |
| 5,382,161 A | 1/1995 | Roane | |
| 5,395,240 A | 3/1995 | Paschke et al. | |
| 5,409,378 A | 4/1995 | Pohl | |
| 5,415,547 A | 5/1995 | Torabinejad et al. | |
| RE35,070 E | 10/1995 | Fitzmorris | |
| 5,464,362 A | 11/1995 | Heath et al. | |
| 5,518,399 A | 5/1996 | Sicurelli, Jr. et al. | |
| RE35,264 E | 6/1996 | Bennett | |
| 5,527,205 A | 6/1996 | Heath et al. | |
| 5,540,766 A | 7/1996 | Castellani | |
| 5,564,929 A | 10/1996 | Alpert | |
| 5,588,835 A | 12/1996 | Kert | |
| 5,595,486 A | 1/1997 | Manocha | |
| 5,605,460 A | 2/1997 | Heath et al. | |
| 5,624,259 A | 4/1997 | Heath et al. | |
| 5,624,976 A | 4/1997 | Klee | |
| 5,628,674 A | 5/1997 | Heath et al. | |
| 5,648,403 A | 7/1997 | Martin | |
| 5,653,590 A | 8/1997 | Heath et al. | |
| 5,655,950 A | 8/1997 | Heath et al. | |
| 5,713,736 A | 2/1998 | Heath et al. | |
| 5,741,139 A | 4/1998 | Sicurelli, Jr. et al. | |
| 5,752,825 A | 5/1998 | Buchanan | |
| 5,762,497 A | 6/1998 | Heath | |
| 5,762,541 A | 6/1998 | Heath et al. | |
| 5,769,638 A | 6/1998 | Torabinejad et al. | |
| 5,797,748 A | 8/1998 | Reynaud et al. | |
| 5,803,736 A | 9/1998 | Merrit, Jr. | |
| 5,807,106 A | 9/1998 | Heath | |
| 5,816,816 A | 10/1998 | Scharf | |
| 5,833,464 A | 11/1998 | Foser | |
| 5,882,196 A | 3/1999 | Kert | |
| 5,915,970 A | 6/1999 | Sicurelli, Jr. et al. | |
| 5,919,044 A | 7/1999 | Sicurelli, Jr. et al. | |
| 5,921,775 A * | 7/1999 | Buchanan | 433/102 |
| 5,925,179 A | 7/1999 | Mannschedel | |
| 5,941,760 A | 8/1999 | Heath et al. | |
| 5,948,129 A | 9/1999 | Nonami et al. | |
| 5,989,032 A | 11/1999 | Reynaud et al. | |
| 6,010,335 A * | 1/2000 | Kert | 433/81 |
| 6,012,924 A | 1/2000 | Reynaud et al. | |
| 6,024,565 A | 2/2000 | Sicurelli et al. | |
| 6,024,569 A * | 2/2000 | Ohne et al. | 433/224 |
| 6,028,125 A | 2/2000 | Combe et al. | |
| 6,030,220 A | 2/2000 | Karmaker et al. | |
| 6,039,569 A | 3/2000 | Prasad et al. | |
| 6,074,209 A | 6/2000 | Johnson | |
| 6,106,296 A | 8/2000 | Johnson | |
| 6,120,294 A | 9/2000 | Engelbrecht et al. | |
| 6,126,446 A | 10/2000 | Mannschedel | |
| 6,162,056 A | 12/2000 | Mannschedel | |
| 6,183,253 B1 * | 2/2001 | Billet et al. | 433/81 |
| 6,220,863 B1 | 4/2001 | Kamohara et al. | |
| 6,224,377 B1 | 5/2001 | Bachmann | |
| 6,254,392 B1 | 7/2001 | Mannschedel et al. | |
| 6,261,099 B1 | 7/2001 | Senia et al. | |
| 6,264,471 B1 * | 7/2001 | Martin | 433/224 |
| 6,267,597 B1 * | 7/2001 | Kim | 433/224 |
| 6,287,122 B1 | 9/2001 | Seeram et al. | |
| 6,293,795 B1 | 9/2001 | Johnson | |
| 6,371,763 B1 | 4/2002 | Sicurelli, Jr. et al. | |
| 6,428,319 B1 * | 8/2002 | Lopez et al. | 433/224 |
| 6,455,608 B1 | 9/2002 | Jia et al. | |
| 6,472,454 B1 | 10/2002 | Qian | |
| 6,537,563 B2 | 3/2003 | Jia et al. | |
| 6,566,418 B2 | 5/2003 | Imai et al. | |
| 6,568,937 B2 | 5/2003 | Kamohara et al. | |
| 6,787,584 B2 | 9/2004 | Jia et al. | |
| 2002/0019456 A1 | 2/2002 | Jia | |
| 2002/0072035 A1 | 6/2002 | Hickok | |
| 2002/0142261 A1 | 10/2002 | Van Den Houdt | |
| 2002/0147249 A1 | 10/2002 | Klee et al. | |
| 2002/0198283 A1 | 12/2002 | Imai et al. | |
| 2003/0045604 A1 | 3/2003 | Klee | |
| 2003/0113686 A1 | 6/2003 | Jia et al. | |
| 2003/0124483 A1 | 7/2003 | Jia et al. | |
| 2003/0207960 A1 | 11/2003 | Jia | |
| 2004/0248067 A1 | 12/2004 | Lopez et al. | |
| 2004/0265783 A1 | 12/2004 | Karmaker et al. | |
| 2005/0003328 A1 | 1/2005 | Karmaker et al. | |

| | | | |
|---|---|---|---|
| 2005/0066854 | A1 | 3/2005 | Jia et al. |
| 2005/0069836 | A1 | 3/2005 | Jia et al. |

FOREIGN PATENT DOCUMENTS

| | | |
|---|---|---|
| DE | 35 04 472 A1 | 7/1986 |
| DE | 35 12 938 A1 | 10/1986 |
| DE | 35 13 864 A1 | 10/1986 |
| DE | 38 39 466 C2 | 6/1989 |
| DE | 41 03 355 A1 | 6/1992 |
| FR | 557756 | 5/1923 |
| FR | 1 180 326 | 12/1958 |
| FR | 2 616 653 | 6/1987 |
| FR | 2 669 211 | 5/1992 |
| FR | 2 730 627 | 8/1996 |
| GB | 1412077 | 10/1975 |
| WO | WO 93/14714 | 8/1993 |
| WO | WO/9319687 | 10/1993 |
| WO | WO98/11842 | 3/1998 |
| WO | WO 00/67659 | 11/2000 |
| WO | WO 2004/037214 A1 | 5/2004 |

OTHER PUBLICATIONS

PCT Written Opinion with date of mailing Jan. 26, 2001.
Notification of Transmittal of the International Preliminary Examining Report with date of mailing Oct. 4, 2001.
Notification of Transmittal of the International Preliminary Examination Report with date of mailing Jan. 24, 2005.
PCT Notification of Transmittal of the International Search Report and the Written Opinion of the International Searching Authority, or the Declaration with date of mailing Apr. 1, 2005.
Soft Core Dental Products Information "Soft Core" [http://www.variodent.at/grossha/022000/soft-core.html] May 2001.
Dentsply Product Information "Thermasystem Plus Obturation System" [http://www.xray.essix.comendodontics/endomain.html] May 2001.
Product Information for Tone P757 Polymer, Form No. 321.00050,Dow Chemical Company, Dec. 2001.
Product Information for Tone P767 Polymer, Form No. 321-00051, Dow Chemical Company, Dec. 2001.
Product Information for Tone P787 Polymer, Form No. 321-00052, Dow Chemical Company, Dec. 2001.
Shipper G., Orstavik D., Teixeira F.B., Trope M., An Evaluation of Microbial Leakage in Roots Filled with a Thermoplastic Synthetic Polymer-Based Root Canal Filling Material (Resilon), Journal of Endodontics, vol. 30, No. 5, May 2004, pp. 342-347.
Teixeira F.B., Teixeira E.C.N., Thompson J.Y., Trope M. "Francture Resistance of Roots Endodontically Treated with a New Resin Filling Material", JADA 2004; 135:646-652.
Nahmais Y., Serota K.S., Watson, Jr. W.R., "Predictable Endodontic Success: Part II—Microstructural Replication", Oral Health Journal, Dec. 2003.
Mounce R., Glassman G., "Bonded Endodontic Obutruation: Another Quantum Leap Forward for Endodontics", Oral Health Jurnal, Jul. 2004.
Goff, S. "Easier Endo, A DPR survey report", Dental Products Report, Sep. 2004, pp. 14,15,16,17,18,20.
Shipper, G., Teixeria, F.B., Arnold, R.R., Trope, M, "Periapical Inflammation after Coronal Microbial Inoculation of Dog Roots Filled with Gutta-Percha or Resilon", Journal of Endodontics, vol. 31, No. 2, Feb. 2005, pp. 91-96.
Chivian N., "Resilon—The Missing Link in Sealing theRoot Canal", Compendium, vol. 25, No. 10A, Oct. 2004, pp. 823-825.
Barnett F., Trope M., "Adhesive Endodontics: Combining Technologies for Enhanced Success", Dentaltown, vol. 5, Issue 8, Aug. 2004, pp. 34,36,38.
Dentsply Product Information "DENSFIL" [http://www.mailefer.com/html/obturation.html] May 2001.

* cited by examiner

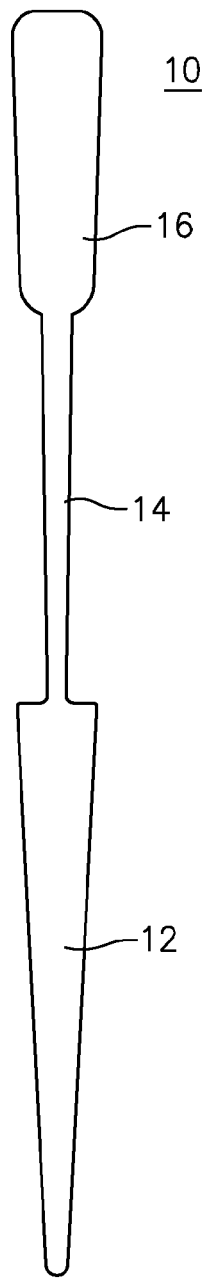
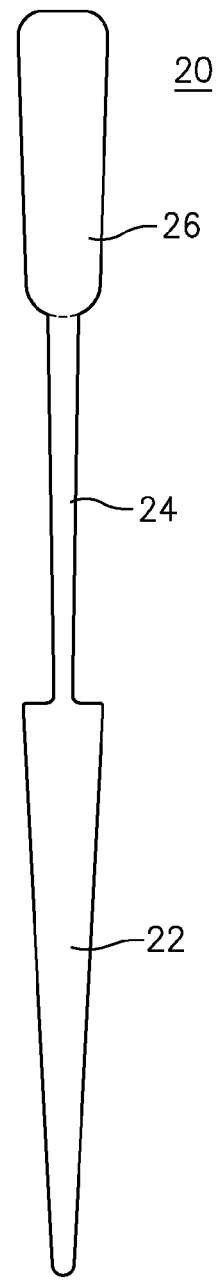
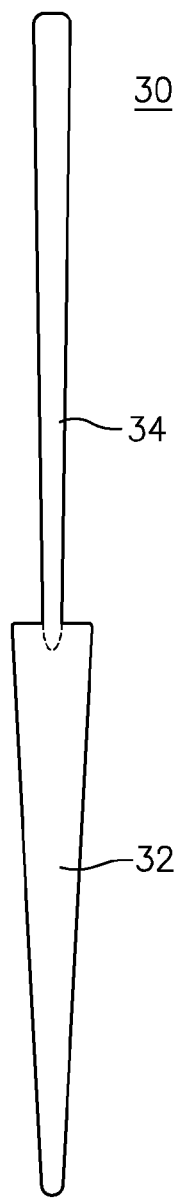
*FIG. 1*  *FIG. 2*  *FIG. 3*

ENDODONTIC OBTURATOR

FIELD OF THE INVENTION

This invention relates to both the obturation of a root canal having undergone endodontic treatment and the simultaneous placement of an endodontic post system.

BACKGROUND OF THE INVENTION

Endodontics or root canal therapy is that branch of dentistry that deals with the diseases of the dental pulp and associated tissues. One aspect of endodontics comprises the treatment of infected root canals, the removal of diseased pulp tissues, followed by the biomechanical modification and the subsequent filling of the pulp canal (root canal). Root canal therapy is generally indicated for teeth having sound external structures but having diseased, dead or dying pulp tissues. Such teeth may or may not generally possess intact enamel and dentin and are satisfactorily engaged with bony tissue. In such teeth, the pulp tissue and excised portions of the root should be replaced by a biocompatible substitute.

One technique for the preparation of a root canal involves creating a coronal access opening with a conventional dental drill. A tool is used for gross removal of pulp material from the root canal through the coronal access opening. The void formed is enlarged with reamers and/or files to result in a fully excavated cavity. Debris is removed from this cavity by flushing and the cavity is cleansed to remove all diseased tissue. Following chemical antisepsis, the excavated canal is ready for filling.

A basic method involves inserting a filling cone into a root canal and cementing therein to obturate the canal. Lateral condensation is a method in which several filling cones, a primary cone and auxiliary cones, are inserted into a root canal. The primary cone is inserted and cemented to the seat of the root canal. Using a tapered spreader, the primary cone is then squeezed against the side of the root canal and a second cone is inserted and cemented into place. This process is continued until the root canal is completely obturated which can require up to 10 to 15 filling cones. Vertical condensation of warm or hot gutta percha is yet another method of sealing root canals. After cementing a primary cone short of the apex of the root canal, heat application is alternated with a series of smaller and smaller pluggers until the gutta percha is moved to the apex. This is often possible when the smallest plugger approaches the apex of the tooth within 3 to 5 millimeters. The space is then backfilled. Lateral canals are packed and sealed as a consequence of lateral expansion of a wave of heated gutta percha. Alternatively, small segments of gutta percha can be used in this method that are inserted into the root canal, heated in order they can adhere to one another and each backfilled one at a time until the root canal is filled. All three of these methods, the single filling cone, lateral condensation and vertical condensation apply root canal cement or sealer around the individual cones or in between segments as a binding agent.

Another method employs an injection gun that injects warm or hot gutta percha filling material into a root canal. The injector initially places heated gutta percha at the seat of the root canal which is then condensed with a plugger into the root tip. The injector then backfills the root canal by injecting additional gutta percha into the root canal until it is obturated. A similar method involves heating gutta percha on a flexible metal carrier used to insert the gutta percha into the root canal. The carrier may be a solid rod, or a hollow rod, situated in the center of a master cone. The rod is connected to a handle which may be removed by slipping it out of the hollow rod, or cutting it off if it is a solid rod. While these systems provide for convenient and quick obturation of the canal, they pose a removal problem for the dentist who has to place a post.

Of all the methods used for obturating a canal, there is no device currently available that will allow a doctor to simultaneously obturate a root canal and place an endodontic post. Currently, an endodontist will perform the root canal procedure and the obturation during one patient visit. After the canal is obturated and temporarily sealed, the patient is frequently treated by a second dentist who will place the post. To do so, the gutta percha has to be removed from the canal until only a portion 5 mm or so from the apex remains to act as an apical seal. The rods inside the current systems make gutta percha removal much more difficult since the coronal portion of the gutta percha rod has to be removed to allow for the placement of the endodontic post. One way to overcome this problem has been to notch the obturating rod with a bur. Then, when the obturator is placed in the canal it is twisted, snapping off the apical portion. The longer coronal portion is removed. It is then re-introduced into the canal and the gutta percha is stripped off by means of pulling the rod through an endodontic stop. Since the endodontic stop is extremely narrow, the gutta percha is pulled from the rod as it is withdrawn and the gutta percha remains in the canal. It is subsequently condensed. As a result of this technique, the restoring dentist does not have to deal with the rod and only has to remove the gutta percha to make room for the post. Some gutta percha may remain on the walls of the canal jeopardizing the bond strength of the post to the radicular dentin. Reinfection of the treated tooth can be a problem because the endodontist performing the root canal procedure will seal the coronal opening with a temporary stopping agent which can leak oral fluids carrying bacterial into the canal opening.

Currently, endodontic obturators are made of a shaft having a distal end covered with a filler material such as gutta percha. The shaft material is typically made of metal or plastic and may not be completely compatible with gutta percha. This can cause leakage at the interface of the shaft and the gutta percha material. Moreover, the gutta percha material tends to be brittle in nature and can cause failure of the filler material when the appliance exhibits a curvature. Appliances having curvatures are required when obturating root canals that are not straight.

It is desirable to reduce and/or eliminate the leakage problems associated with poor sealing at the coronal end of the canal. It would be preferable to provide an appliance that is compatible with the filler material. It would be beneficial to provide an appliance that would possess sufficient flexibility to minimize the risk of premature failiure when the canal exhibits a curvature.

SUMMARY OF THE INVENTION

These and other objects and advantages are accomplished by the endodontic obturator of the present invention comprising a shaft section and a filler section fabricated of the same material and formed as a single unit. A handle section may be included and may be formed integrally with the shaft section and filler section as a single unit, or may be fabricated separately and attached to the single unit containing the shaft section and the filler section.

In another embodiment herein, an endodontic post is provided having a post section and a filler section fabricated of the same matrix material to provide a cohesive bond between the two sections.

BRIEF DESCRIPTION OF THE DRAWINGS

Features of the present invention are disclosed in the accompanying drawings, whrerein similar reference characters denote similar elements throughout the several views, and wherein:

FIG. 1 is an elevational view of an obuturator in accordance with the invention;

FIG. 2 is an elevational view of an alternate obuturator in accordance with the invention; and FIG. 3 is an elevational view of a post in accordance with the invention.

DESCRIPTION OF THE INVENTION

As will be appreciated, the present invention provides an endodontic obturator having a shaft section and a filler section fabricated of the same material and formed as a single unit. The shaft section comprises the filler section as an integral part of the shaft section. A handle section may be included and may be formed integrally with the shaft section and filler section as a single unit, or may be fabricated separately and attached to the single unit containing the shaft section and the filler section.

Reference is made to FIG. 1, which shows an obturator 10. The obturator contains a filler section 12, a shaft section 14 and a handle section 16. The filler section 12, shaft section 14 and handle section 16 are a single unit component. The obturator is manufactured as a single one-piece unit. Preferably, the unit is molded in a single mold having multiple cavities. Alternatively, the handle section 26 may be molded separately from the filler section 22 and shaft section 24 as shown in the obturator 20 in lower halves of the shafts sections. The lower halves of shaft sections 14 and 24 act as filler sections 12 and 22, respectively. The obturators herein may be manufactured by any known method in the art and depending upon the material used for the manufacture. Such methods include but are not limited to matched die processes, autoclave molding, resin injection molding (RIM), sheet, dough and bulk molding, press molding, injection molding, reaction molding, resin transfer molding (RTM), compression molding, open molding, hand rolling, dipping and rolling, pressing, extrusion, pultrusion and filament winding. Alternatively, a rod shaped material may be manufactured and thereafter shaped by grinding, cutting, milling or the like into the desired shape and size.

The shaft, filler and handle sections are manufactured of the same material when manufactured as a single unit. The material may include any biocompatible material for filling the apex of the canal that is also strong enough to withstand forces encountered by the shaft section. The material is typically a thermoplastic, chemo-plastic (i.e., may be softened by chemicals), synthetic rubber, resinous or similar polymeric material. Examples of thermoplastic materials include but are not limited to polyacrylates such as polymethyl methacrylate, polyhydroxy ethyl methacrylate, and hydroxy ethyl methacrylate (HEMA), polyurethanes, polypropylene, polyethylene, polyamides, fluoropolymers such as Teflon® PTFE and Teflon® PFA, polyesters such as polylactic acid, glycolide and polycaprolactone and their co-polymers, polyphosphazenes, polyanhydrides, polysulfides, polyethers, epoxies, polycarbonates, polystyrene, polybutadiene, polyphenylene oxide, and synthetic rubber materials and silicone rubber materials such as polysiloxanes. Examples of additional polymeric materials include, but are not limited to, polyarylates, styrene acrylonitriles, ABS polymers, polysulfones, polyacetals, polyphenylene sulfides, polyarylsulfides, acrylonitrile-butadiene-styrene copolymers, polyurethane dimethacrylates (hereinafter abbreviated to PUDMA), and the like.

Alternatively, the handle may be manufactured of a different material that cohesively bonds to the material of the shaft and filler sections. The material may include, but is not limited to, any of the materials described above for the manufacture of the shaft and filler sections. Moreover, the handle may be fabricated of any other thermoplastic or thermoset material including, but not limited to, epoxies, polyester, vinyl esters and their composites.

The material used to fabricate the shaft, filler and optionally the handle section may include additives typical in the dental field such as plasticizing, antibiotic, cariostatic, antibacterial, or other anti-inflammatory, biologically active or therapeutic materials.

In another embodiment herein, an endodontic post is provided having a post section and a filler section. FIG. 3 shows an endodontic post having filler section 32 and post section 34. Filler section 32 and post section 34 are fabricated of the same matrix material to provide a cohesive bond between the two sections. The matrix material is any biocompatible material for filling the apex of the canal. The material is typically a thermoplastic, synthetic rubber, chemo-plastic (i.e., may be softened by chemicals), resinous or similar polymeric material. Examples of thermoplastic materials include but are not limited to polyacrylates such as polymethyl methacrylate, polyhydroxy ethyl methacrylate, and hydroxy ethyl methacrylate (HEMA), polyurethanes, polypropylene, polyethylene, polyamides, fluoropolymers such as Teflon® PTFE and Teflon® PFA, polyesters such as polylactic acid, glycolide and polycaprolactone and their co-polymers, polyphosphazenes, polyanhydrides, polysulfides, polyethers, epoxies, polycarbonates, polystyrene, polybutadiene, polyphenylene oxide, and synthetic rubber materials and silicone rubber materials such as polysiloxanes. Examples of polymeric materials include, but are not limited to, polyarylates, styrene acrylonitriles, ABS polymers, polysulfones, polyacetals, polyphenylene sulfides, polyarylsulfides, acrylonitrile-butadiene-styrene copolymers, polyurethane dimethacrylates (hereinafter abbreviated to PUDMA), and the like.

The post section 34 is fabricated of the same matrix material, but may also include reinforcing materials to provide sufficient strength to withstand forces exerted on posts in root canals. Reinforcing materials include, but are not limited to, filler and fiber materials. The fibers may be present in the form of long, unidirectional, continuous filaments which are preferably at least partially aligned and oriented along the longitudinal dimension of the component with alignment normal or perpendicular to that dimension also possible. The fibers may be of uniform or random length, unidirectional or multidirectional, or randomly dispersed, and may be as short as about 3 to about 4 millimeters (mm) or shorter. The fibers may also be in the form of fabric as set forth in U.S. Pat. No. 6,186,791, and may include any of the attributes of the post described therein, the contents all of which are hereby incorporated by reference. Due to the improved structural integrity, the amount of fibers in the structural component preferably equals at least about 20% by weight (wt %) and preferably about 20 wt % to about 70 wt %. Possible reinforcing fibers, which are preferably used in accordance with U.S. Pat. Nos. 4,717,341 and 4,894,012 to Goldberg et al. (which are herein incorporated by reference), include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. One preferred version of the device is comprised of unidirectional microfilamentous glass fibers bundled in a resin matrix.

Fillers may be present in addition to or instead of fibers in an amount up to about 80 wt %, and preferably about 70 wt %. If fibers are present, the amount of filler is present in an amount of up to about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, barium sulfate, bismuth oxychloride, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates. If the post section is manufactured from a composite material, it is preferably in completely cured or hardened state.

In accordance with one method of manufacture herein, post section 34 and filler section 32 are manufactured by any known method in the art and depending upon the material used for the manufacture thereof. Such methods include but are not limited to matched die processes, autoclave molding, resin injection molding (RIM), sheet, dough and bulk molding, press molding, injection molding, reaction injection molding, resin transfer molding (RTM), compression molding, open molding, hand rolling, dipping and rolling, pressing, extrusion, pultrusion and filament winding. Alternatively, a rod shaped material may be manufactured and thereafter shaped by grinding, cutting, milling or the like into the desired shape and size of each filler section and post section.

Post section 34 and filler section 32 can be simultaneously injection molded (co-injection molding). Both post section 34 and filler section 32 will be fabricated from matrix polymers of the same or very similar chemical structure. As a result, a cohesive bond can be achieved between post section 34 and filler section 32.

In another method of bonding post section 34 and filler section 32, the sections may be prepared separately and thereafter mechanically joined together. One end of each section will be threaded to join them together. For example, the end of filler section 32 is provided with female threading and the end of post section 32 is provided with male threading. The threads can be obtained by injection molding with appropriate mold designs or by machining the threads after molding.

In order to enhance the bond between the fibers and/or fillers and resin or polymeric matrix of post section 34, thereby enhancing the reinforcing effect, the fibers and/or fillers may be silanized or otherwise treated such as by grafting functional monomers to obtain proper coupling between the fibers and/or fillers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane are A-174 (p-methacrylate propyl tri-methoxy silane), produced by OSI Specialties, New York and SIA0591 N-(2-aminoethyl)-3-aminopropyl trimethoxysilane, produced by Gelest, Tullytown, Pa.

The matrix material may include polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Filler section 32 is preferably in the conically-shaped to fit appropriately in the canal. Post section 34 may be of any surface (e.g., smooth, partly smooth and partly frustoconical,) and shape suitable for placement in the canal.

The post may be provided in an opaque tooth color or it may be colored similar to a tooth's pulp for enhanced esthetics. The post may include an appropriate amount of radiopaque material such as titanium oxide, barium sulfate, and similar materials known in the dental industry to insure x-ray documentation which may be added to the post material during manufacture thereof.

The length of post unit 30 may vary depending upon the length of the root into which it will be inserted. It is preferable that post 30 be manufactured in a variety of lengths and widths to fit the many different root canals of dental patients and the differing lengths of the anterior (central and lateral incisors, bicuspids and premolars) and molar teeth. Preferably, post unit 30 is about 14 to about 31 mm in length and more preferably about 16 to about 25 mm in length. The post section 34 and filler section 32 are somewhat flexible to negotiate curved canals. More preferably, filler section 32 is more flexible than post section 34.

The tip of post section 34 that is inside filler section 32 as shown in FIG. 3 will vary and range from about 0.15 to about 0.5 and preferably from about 0.2 to about 0.3. At the supracoronal end, the diameter is about 0.4 to about 2.0 and preferably about 0.5 to about 1.75 mm.

Filler section 32 is between about 4 to about 15 mm in length. Filler section 32 can be tapered at least 0.02 mm/per mm in accordance with ISO standards, and preferably 0.04 or 0.06 mm/per mm, or greater, measuring from apical tip to the upper end which connects to post section 34. The diameter of the apical end of filler section 32 is in the range of about 0.20 to about 2.0 mm and preferably 0.25 to about 0.8 mm. The diameter of the upper end of filler section 32 that connects to post section 34 is in the range of about 0.20 to about 2.0 mm and preferably about 0.28 to about 1.17 mm. When using the post unit in canals of 0.02 taper, the filling material such as a thermoplastic material will be compressed by the canal and forced toward the coronal end of the canal. This will result in an apical seal in excess of 8 mm. The excess thermoplastic material can be removed with a heated instrument after it has hardened. When using the post unit in 0.06 tapered canals, the filling material can be condensed down toward the apex to fill the void created by the greater taper. This will result in an apical seal less than 8 mm, but in excess of 4 mm, which is sufficient to maintain the apical seal.

To use the post unit, the device can be placed in or near an oven or heater to heat and soften the filling material or dipped in a chemical solution such as chloroform to soften the filling material. The device will then be placed in a root canal that has been opened to a predetermined dimension by use of endodontic files, to seal the apical end. If necessary, the filling material can be compacted toward the apex, while it is still in the softened state, to ensure the apex is adequately sealed. The post is then cemented into place by lining the canal walls with a bonding agent and filling the interface between the post and the walls of the canal with a resin cement, such as a dual cure cement. This will result in a coronal seal of the canal via resin restorative material and an apical seal of the canal by means of the filling material and sealant.

The softening of the filling material by heat or with chemical means can be avoided if the prepared root canal is filled with a flowable root canal sealant such as FibreFill R.C.S., marketed by Pentron Clinical Technologies, LLC, Wallingford, Conn., before placing the obturator post. The canal should be filled sufficiently so that the obturator, when placed into the canal, will displace enough sealant to fill the canal completely. The apical end of the obturator post is coated with a sealant and inserted into the root canal. The sealant is then cured by light.

In both techniques, the remaining portion of the post, extending supra-gingivally, will be used to build a core around it, and if necessary, for placement of a crown thereon. Any excess of the post will be cut off. The device may be provided in a variety of lengths to accommodate longer roots in anterior teeth and smaller roots in the molar region.

Examples of more flexible materials used herein in comparison to current gutta percha are given in Table 1 below. The results were obtained by tensile test as per ASTM D638.

TABLE 1

| Material | Tensile Strength (PSI) | Elongation at Break (%) | Filler |
|---|---|---|---|
| Gutta Percha | 1290 ± 34 | 4 ± 1 | Zinc oxide, barium sulfate |
| PE-Blend1 | 2800 ± 9 | 38 ± 5 | 40% by weight barium sulfate |
| PE-Blend2 | 2100 ± 22 | 91 ± 4 | 40% by weight bismuth oxychloride |

The matrix materials of PE-Blend1 and PE-Blend2 are high density polyethylene (BP Solvay, Houston, Tex.), and low density polyethylene (Huntsman Polymers, Houston, Tex.) respectively. The filler content of current gutta percha is not revealed by its manufacturer. As can be seen from Table 1, the tensile strength and elongation at break of both polyethylene blends are much higher than those of current gutta percha. Therefore, the new blends are much stronger and flexible than current gutta percha.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An appliance for applying a filler material to a root canal comprising:
   an elongated body having a proximal handle portion and a distal shaft portion;
   whereby the shaft portion may be inserted in a root canal;
   whereby the shaft portion comprises a filler material portion as an integral part of the shaft portion;
   wherein the filler material portion has a greater width than the shaft portion that connects the filler material portion to the handle portion;
   wherein the handle portion has a greater width than the shaft portion to which the handle is connected;
   wherein the shaft and entire filler material portions are fabricated from a first material as a single one-piece unit;
   wherein the handle portion is manufactured from a second material that is different than the first material; and
   wherein the second material is a material that cohesively bonds to the first material.

2. The appliance of claim 1 wherein the shaft portion and the entire filler material portion are fabricated of a thermoplastic material or a synthetic rubber material.

3. The appliance of claim 2 wherein the synthetic rubber material comprises a silicone rubber material.

4. The appliance of claim 3 wherein the silicone rubber materials comprise polysiloxanes.

5. The appliance of claim 2 wherein the shaft portion and the entire filler material portion are fabricated of polysiloxanes, styrene-butadiene, ethylene-propylene, polysulfones, polyacrylates, polyisoprenes, epicholorohydrin, polyacetals, polyphenylene sulfides, polyarylsulfides, polyurethane dimethacrylate (PUDMA), styrene acrylonitrile, acrylonitrile-butadiene-styrene (ABS) polymers or mixtures thereof.

6. The appliance of claim 2 wherein the shaft portion and the entire filler material portion are fabricated of polyarylates, polyurethanes, polypropylenes, polyethylenes, polyamides, polyimides, fluoropolymers, polyesters, polyphosphazenes, polyanhydrides, polysulfides, polyethers, epoxies, polycarbonates, polystyrenes, polybutadienes, polyphenylene oxides or mixtures thereof.

7. The appliance of claim 6 wherein the polyacrylates are selected from the group consisting of polymethyl methacrylate, polyhydroxy ethyl methacrylate, and hydroxy ethyl methacrylate (HEMA).

8. The appliance of claim 6 wherein the fluoropolymers are selected from the group consisting of Teflon® polytetraflouethylene (PTFE) and Teflon® perflouroalkoxy (PFA).

9. The appliance of claim 6 wherein the polyesters are selected from the group consisting of polylactic acid, glycolide, polycaprolactone and co-polymers thereof.

10. The appliance of claim 1 wherein the shaft portion and the entire filler material portion are fabricated of a polymeric or resinous material.

11. The appliance of claim 1 wherein the handle portion is fabricated from a thermoplastic, thermoset material or synthetic rubber material.

12. The appliance of claim 11 wherein the synthetic rubber material comprises silicone rubber materials.

13. The appliance of claim 12 wherein the silicone rubber materials comprise polysiloxanes.

14. The appliance of claim 11 wherein the handle portion is fabricated of polysiloxanes, styrene-butadiene, ethylene-propylene, polysulfones, polyacrylates, polyisoprenes, epicholorohydrin, polyacetals, polyphenylene sulfides, polyarylsulfides, polyurethane dimethacrylate (PUDMA), styrene acrylonitrile, acrylonitrile-butadiene-styrene (ABS) polymers or mixtures thereof.

15. The appliance of claim 14 wherein the polyacrylates are selected from the group consisting of polymethyl methacrylate, polyhydroxy ethyl methacrylate, and hydroxy ethyl methacrylate (HEMA).

16. The appliance of claim 11 wherein the thermoset material comprises an epoxy material.

17. The appliance of claim 1 wherein the handle portion is fabricated of a polymeric or resinous material.

18. The appliance of claim 1 wherein the handle portion is fabricated of polyarylates, polyurethanes, polypropylenes, polyethylenes, polyamides, polyimides, fluoropolymers, polyesters, polyphosphazenes, polyanhydrides, polysulfides, polyethers, epoxies, polycarbonates, polystyrenes, polybutadienes, polyphenylene oxides, vinyl esters or mixtures thereof.

19. The appliance of claim 18 wherein the fluoropolymers are selected from the group consisting of Teflon® polytetraflouethylene (PTFE) and Teflon® perflouroalkoxy (PFA).

20. The appliance of claim 18 wherein the polyesters are selected from the group consisting of polylactic acid, glycolide, polycaprolactone and co-polymers thereof.

21. The appliance of claim 1 wherein the shaft and entire filler portions are fabricated of a material comprising plasticizing, antibiotic, cariostatic, antibacterial, anti-inflammatory, biologically active, therapeutic materials or mixtures thereof.

22. The appliance of claim 1 wherein the handle portion is fabricated of a material comprising plasticizing, antibiotic, cariostatic, antibacterial, anti-inflammatory, biologically active, therapeutic materials or mixtures thereof.

23. An endodontic post comprising:
a filler section and a post section;
whereby the filler section and the post section both comprise the same matrix material;
whereby the post section further comprises a reinforcing material dispersed in the matrix material;
whereby the filler section does not include a reinforcing material dispersed in the matrix material;
whereby the filler and post sections are provided in hardened, solid form; and
whereby the post can support a core thereon.

24. The endodontic post of claim 23 wherein the matrix material is a thermoplastic material or synthetic rubber material.

25. The endodontic post of claim 23 wherein the matrix material is a resinous or polymeric material.

26. The endodontic post of claim 23 wherein the matrix material comprises polyarylates, polyurethanes, polypropylenes, polyethylenes, polyamides, polyimides, fluoropolymers, polyesters, polyphosphazenes, polyanhydrides, polysulfides, polyethers, epoxies, polycarbonates, polystyrenes, polybutadienes, polyphenylene oxides or mixtures thereof.

27. The endodontic post of claim 26 wherein the fluoropolymers are selected from the group consisting of Teflon® polytetraflouethylene (PTFE) and Teflon® perflouroalkoxy (PFA).

28. The endodontic post of claim 26 wherein the polyesters are selected from the group consisting of polylactic acid, glycolide, polycaprolactone and co-polymers thereof.

29. The endodontic post of claim 23 wherein the synthetic rubber material comprises a silicone rubber material.

30. The endodontic post of claim 29 wherein the silicone rubber material comprises polysiloxanes.

31. The endodontic post of claim 23 wherein the matrix material comprises polysiloxanes, styrene-butadiene, ethylene-propylene, polysulfones, polyacrylates, polyisoprenes, epicholorohydrin, polyacetals, polyphenylene sulfides, polyarylsulfides, polyurethane dimethacrylate (PUDMA), styrene acrylonitrile, acrylonitrile-butadiene-styrene (ABS) polymers or mixtures thereof.

32. The endodontic post of claim 31 wherein the polyacrylates are selected from the group consisting of polymethyl methacrylate, polyhydroxy ethyl methacrylate, and hydroxy ethyl methacrylate (HEMA).

33. The endodontic post of claim 23 wherein the matrix material comprises plasticizing, antibiotic, cariostatic, antibacterial, anti-inflammatory, biologically active, therapeutic materials or mixtures thereof.

34. The endodontic post of claim 23 wherein the reinforcing material comprises fillers, fibers or mixtures thereof.

35. The endodontic post of claim 34 wherein the fillers comprise silica, silicate glass, quartz, barium silicate, strontium silicate, barium borosilicate, barium sulfate, bismuth oxychloride, strontium borosilicate, borosilicate, lithium silicate, amorphous silica, ammoniated or deammoniated calcium phosphate and alumina, zirconia, tin oxide, titania or mixtures thereof.

36. The endodontic post of claim 34 wherein the fibers comprise glass, ceramic, metal, carbon, graphite, polymeric such as cellulose, polyamide, aramid, polyester, polyaramid, acrylic, vinyl and modacrylic, polyolefin, polytetrafluorethylene, or mixtures thereof.

37. The endodontic post of claim 34 wherein the fibers comprise long, unidirectional, continuous filaments which are preferably at least partially aligned and oriented along the longitudinal dimension of the post.

38. The endodontic post of claim 34 wherein the fibers are aligned perpendicular to the longitudinal dimension of the post.

39. The endodontic post of claim 34 wherein the fibers comprise random- length fibers.

40. The endodontic post of claim 34 wherein the fibers comprise uniform-length fibers.

41. The endodontic post of claim 34 wherein the fibers comprise randomly dispersed fibers.

42. The endodontic post of claim 34 wherein the fibers comprise fabric.

43. The endodontic post of claim 23 wherein the reinforcing material is surface treated.

44. The endodontic post of claim 23 wherein the reinforcing material is surface treated with a silane.

45. The endodontic post of claim 44 wherein the silane comprises 3-methacryloxypropyl tri-methoxy silane, N-(2-aminoethyl)-3-aminopropyl trimethoxysilane, or a mixture thereof.

46. The endodontic post of claim 23 wherein the matrix comprises polymerization initiators, polymerization accelerators, ultra-violet light absorbers, anti-oxidants, fluorescent whitening agents, free radical initiators, or mixtures thereof.

47. An endodontic post comprising:
a filler section and a post section;
whereby the filler section and the post section both comprise the same matrix material;
whereby the post section further comprises a reinforcing material dispersed in the matrix material;
whereby the matrix material is a thermoplastic material or a synthetic rubber material;
whereby the filler section does not include a reinforcing material dispersed in the matrix material;

whereby the filler and post sections are provided in hardened, solid form;

whereby the post can support a core thereon.

48. An endodontic post comprising:

a filler section and a post section;

whereby the filler section and the post section both comprise the same matrix material;

whereby the post section further comprises a reinforcing material dispersed in the matrix material;

whereby the matrix material is a resinous or polymeric material;

whereby the filler section does not include a reinforcing material dispersed in the matrix material;

whereby the filler and post sections are provided in hardened, solid form;

whereby the post can support a core thereon.

* * * * *